United States Patent
Peter et al.

(10) Patent No.: US 6,933,398 B2
(45) Date of Patent: Aug. 23, 2005

(54) PROCESS FOR THE TRANSESTERIFICATION OF FAT AND/OR OIL BY MEANS OF ALCOHOLYSIS

(76) Inventors: Siegfried Peter, Lindenweg 3, 91080 Uttenreuth (DE); Eckhard Weidner, Am Dorfweiher 9, 91056 Erlangen (DE)

( * ) Notice: Subject to any disclaimer, the term of this patent is extended or adjusted under 35 U.S.C. 154(b) by 191 days.

(21) Appl. No.: 10/669,617

(22) Filed: Sep. 24, 2003

(65) Prior Publication Data

US 2004/0059143 A1 Mar. 25, 2004

Related U.S. Application Data

(63) Continuation of application No. PCT/EP02/07311, filed on Jul. 2, 2002.

(30) Foreign Application Priority Data

Jul. 6, 2001 (DE) .......................................... 101 32 842

(51) Int. Cl.⁷ ................................................. C11C 1/00
(52) U.S. Cl. ....................................................... 554/169
(58) Field of Search .................................. 554/169, 168

(56) References Cited

U.S. PATENT DOCUMENTS 5,354,878 A * 10/1994 Connemann et al. ....... 554/168

* cited by examiner

*Primary Examiner*—Deborah D. Carr
(74) *Attorney, Agent, or Firm*—Webb Ziesenheim Logsdon Orkin & Hanson, P.C.

(57) ABSTRACT

The present invention relates to a process for obtaining fatty acid esters from triglycerides by means of alcoholysis. In particular, the invention relates to a process for the transesterification of fat and/or oil by alcoholysis wherein, in order to accelerate the process in the initial stage, at least one alkanol fatty acid ester is added in a quantity such that the reaction mixture produced thereby consists of one phase. A high reaction rate can thereby be maintained in the process from the beginning.

25 Claims, No Drawings

PROCESS FOR THE TRANSESTERIFICATION OF FAT AND/OR OIL BY MEANS OF ALCOHOLYSIS

CROSS-REFERENCE TO RELATED APPLICATIONS

This application is a continuation of International Patent Application Number PCT/EP02/07311 filed Jul. 2, 2002, entitled "Method For Transesterification Of Fats And/Or Oils By Means Of Alcoholysis" and designating, inter alia, the United States, which claims priority to German Patent Application Serial No. 101 32 842.7, filed Jul. 6, 2001.

BACKGROUND OF THE INVENTION

1. Field of the Invention

The present invention relates to a process of obtaining fatty acid esters from triacylglycerides by means of alcoholysis.

2. Description of the Related Art

Transesterification reactions are well known. They are a commercially important class of industrial organic reactions. In a transesterification reaction, an ester is converted into a different ester by exchange of the acid groups or by exchange of the alcoholic groups. If this transesterification is carried out by exchange of the alcoholic groups, it is termed alcoholysis (also alkanolysis). In alcoholysis, the alcohol or the alkanol is added in excess in order to obtain a high yield of the desired ester. Recently the production of alkyl esters, in particular methyl esters, from vegetable oils (for example, rapeseed oil, soybean oil) has become extremely popular in connection with the production of diesel fuel from renewable raw materials.

Transesterification is an equilibrium reaction which is usually initiated simply by mixing the reactants. The reaction proceeds so slowly, however, that a catalyst is usually necessary in order for the reaction to be carried out commercially. Strong acids or strong bases generally serve as catalysts.

Fats and oils consist mainly of glycerides (mono-, di- and triglycerides). In the transesterification of such fats and oils, low-molecular monohydric alcohols can be substituted for the glycerol component. Here, the method of Bradshaw (described in U.S. Pat. Nos. 2,271,619 and 2,360,844) is frequently employed in practice. The reaction is carried out in an open vessel, which can consist of ordinary carbon steel. The fat or oil must be dry (moisture-free), clean and above all neutral, i.e. the content of free fatty acids must be negligibly low (acid value not higher than 1.5). In general, the monohydric alcohol is added in large excess to the reaction mixture in order to increase the yield and the reaction rate (the equivalent ratio is often greater than 1:6).

In a paper by Wright et al. (H. J. Wright, J. B Segur, H. V. Clark, S. K. Coburn, E. E. Langdon and R. N. DuPuis, Oil & Soap, 21 [1944] 145–148), the precise conditions for the alcoholysis of fats with methanol and ethanol were investigated in detail. The authors also describe experiments with alcoholysis using other monohydric alcohols. It is explained that the above-mentioned alcoholysis catalysed by alkali is completely successful only if the fat is virtually free of free fatty acids and the reaction mixture is free of water. If one of these conditions is not met, saponification takes place; this results in a loss of alkalinity and in the formation of a gel structure, which prevents or retards the separation and precipitation of the glycerol.

Transesterification of triacylglycerides by means of alcoholysis is a reaction between alkanol and triacylglycerides which requires an induction stage, during which there is a low reaction rate because the alkanol reaction component is not soluble in the oil. This situation is very troublesome, especially during the production of methyl esters, because methanol is only slightly soluble in the oils and fats which are to be transesterified. However, methanol is readily soluble in the methyl esters of the fatty acids. Owing to the low concentration of methanol in the oil, the transesterification reaction always proceeds slowly. The reaction mixture has to be mixed vigorously until ultimately the ester content has increased to such an extent that the reaction mixture consists of one phase, at which time the reaction rate rises considerably.

In practice, alkali metals, or alcoholates of the alkali metals, are used as catalysts. The alkaline catalysts dissolve in the reaction mixture, i.e., the reaction is catalysed homogeneously. During the reaction, the alkali metals and their alcoholates are converted to soaps, which dissolve particularly in the glycerol formed and increase the cost of its further processing in order to obtain pure glycerol. However, the methyl ester also retains small quantities of alkali, which may not be completely without problems when methyl esters are used as diesel fuel. Because of this, heterogeneously catalysed processes have also been proposed recently; for example, using a metal salt of a strongly basic amino acid as a solid catalyst which is insoluble in the reaction mixture (Patent Application DE 199 50 593 A1). Furthermore, a catalyst based on titanium oxides has been developed, the disadvantage of which is that the reaction temperatures are in the region of 240° C.

SUMMARY OF THE INVENTION

The present invention relates to a process for the transesterification of fat and/or oil by alcoholysis wherein, in order to accelerate the process in the initial stage, at least one alkanol fatty acid ester is added in a quantity such that the action mixture produced thereby consists of one phase.

The object of the present invention is to eliminate or to shorten the induction stage of transesterification of fat and/or oil by alcoholysis, while maintaining moderate reaction temperatures, thereby rendering the process more effective.

This object is achieved by a process for the transesterification of fat and/or oil by means of alcoholysis, wherein an alkanol, in particular a monohydric alkanol, is added in excess to the fat and/or oil to be transesterified. In particular, at least one alkanol fatty acid ester is added to the fat and/or oil in a quantity such that the reaction mixture produced thereby consists of one phase under the reaction conditions.

Surprisingly, it has now been found that only a small quantity of added alkanol fatty acid esters are needed to achieve this objective. The addition of the alkanol fatty acid esters may take place before, after, or at the same time as the addition of the alkanol. In the process of the present invention, therefore, the initial stage of the transesterification is avoided or shortened.

DETAILED DESCRIPTION OF THE INVENTION

In one embodiment of the present invention, alcoholysis is carried out by using methanol, and adding a portion of the continuously produced methyl esters to the triacylglyceride starting product in quantities such that the mixture of oil, methanol and methyl esters consists of one reaction phase. If the reaction mixture takes place in one reaction phase, the active alkanol concentration is high from the very beginning and the reaction proceeds correspondingly rapidly. For example, at 135° C., in the initial stage of a process heterogeneously catalysed by zinc arginate (production of methyl esters from palm oil), a reaction rate of 0.8 g/skg$_{Znarg}$ was recorded and, after a single phase had formed, a reaction rate of 2.5 g/skg$_{Znarg}$ was recorded.

The fat and/or oil used in the process according to the invention may, in particular, be of biological origin.

The quantity of alkanol fatty acid esters which has to be added in order to produce a one-phase mixture depends on the quality of the oil, the amount of the excess of alkanol and the reaction temperature. The excess of alkanol is generally added in an equivalent ratio (i.e. ratio of mol fatty acids in the fat and/or oil to mol mono-hydric alcohol) of 1:6 or more to increase the reaction rate and the yield of fatty acid alkanol esters.

Alkanol fatty acid esters preferably introduced into the process are, for example, methyl esters, ethyl esters and/or propyl esters.

The alkanol fatty acid esters are added preferably in a quantity of 5 to 50 wt. %, and more preferably 12 to 20 wt. %, based on the fat and/or oil.

The process according to the invention is particularly effective if it is intended to carry out the transesterification in a heterogeneously catalysed process, which is preferably continuous. But the process according to this invention is advantageous even in the case of a homogeneously catalysed process, because the costs of vortexing the two phases in the initial stage of the reaction can be saved. Such heterogeneously catalysed processes are described, for example, in the above-mentioned DE 199 50 593.

Thus, in another preferred embodiment, a catalyst, which may be either a soluble catalyst or a metal salt of an amino acid or of an amino acid derivative which is insoluble in alkanols and in the reaction mixture, is added to the process.

The dissolved catalyst may, for example, be dissolved alkali metals or alcoholates of alkali metals.

The insoluble catalyst may contain a metal component, which is calcium, strontium, barium, another alkaline-earth metal, or a heavy metal, in particular silver, copper, zinc, manganese, iron, nickel, cobalt, lanthanum or another rare-earth metal, while the amino acid component of the insoluble catalyst may contain quaternary nitrogen or a guanidino group. The insoluble catalyst is particularly preferably a heavy metal salt of arginine, in particular the zinc salt or the cadmium salt of arginine. Here, the catalytically active salts which are insoluble in the reaction mixture can be deposited onto a suitable support.

The process according to the invention is carried out particularly effectively if the content of free fatty acids in the fat and/or oil to be transesterified is less than 0.5 wt. %, in particular less than 0.1 wt. %.

It has also been found that the reaction temperatures during the heterogeneously catalysed transesterification should be preferably within the range of 80° C. to 160° C., in particular within the range of 100° C. to 150° C.

Particularly preferably, the process according to the invention is a procedure which includes the recirculation of the alkanol fatty acid esters which remain behind as bottom product following separation of the glycerol from the product flow during the subsequent separation and purification by distillation of the bulk of the methyl esters produced. In this way, small quantities of unreacted glycerides are simultaneously recirculated. Moreover, the glycerol content in the final stage of the reaction is thereby lowered and the yield of the equilibrium reaction is correspondingly increased. Overall, a continuous operation is thus rendered possible.

The preferred quantity of methyl esters for producing a single phase at reaction temperatures within the range of 100° C. to 150° C. is approximately 12 to 20 wt. %.

The process of the present invention is explained in more detailed by the following three working examples, which are contrasted to the one comparative example from the prior art.

Working Example 1

Thus, the process according to the invention was tested on a mixture of sunflower oil and methanol. In this case, at 135° C. and with an equivalent ratio of mol fatty acids in the oil to methanol of 1:6 (60 wt. % sunflower oil and 40 wt. % methanol), an addition of approximately 15 wt. % methyl esters, based on the oil, was sufficient to produce a one-phase system. The pressure established in the case described was 5 bar. Zinc arginate was used as catalyst. The reaction rate was 2.5 g/skg$_{Znarg}$. In this Example, a high reaction rate was maintained from the beginning.

Working Example 2

In addition, palm oil was mixed with methanol at 150° C. in an equivalent ratio of 1:6 and zinc arginate was added as catalyst. After the addition of 20 wt. % methyl esters, based on palm oil, the mixture consisted of one phase. At 3.2 g/skg$_{Znarg}$ the reaction rate was high from the beginning. The initial stage with a low reaction rate was omitted.

Working Example 3

Palm oil was also mixed with methanol at 85° C. in an equivalent ratio of 1:6 and zinc arginate was added as catalyst. The reaction rate was 0.05 g/skg$_{Znarg}$. After a one-phase reaction mixture had been produced by the addition of methylesters (approximately 13 wt. % based on oil), a reaction rate of 0.35 g/skg$_{Znarg}$ was recorded at ambient pressure.

Comparative Example 1

At reaction temperatures of 200° C. to 240° C., in accordance with the process described in the German Patent DE 198 03 053 C1, using zinc soaps as catalysts at pressures of up to 90 bar, triglycerides were converted to esters with a high equivalent excess of methanol (equivalent ratio greater than 1:6). Under these conditions, a higher content of methyl esters is required to produce a onephase system than in the above example at 135° C.

What is claimed is:

1. A process for transesterification of a fat and/or an oil by means of alcoholysis, comprising adding to the fat and/or oil an excess of an alkanol and at least one alkanol fatty acid ester, wherein a reaction mixture is formed, and further wherein an alkanol fatty acid ester is added to the reaction mixture resulting in a one-phase transesterification of the fat and/or an oil.

2. The process of claim 1, wherein the alkanol is mono-hydric alkanol.

3. The process of claim 2, wherein the alkanol fatty acid ester is selected from the group consisting of methyl esters, ethyl esters and propyl esters.

4. The process of claim 3, wherein the alkanol fatty acid ester is added in a quantity of between 5 to 50 wt. % of the fat and/or the oil.

5. The process of claim 3, wherein the alkanol fatty acid ester is added in a quantity of between 12 to 20 wt. % of the fat and/or the oil.

6. The process of claim 3, wherein the mol ratio of the alkanol to the fat and/or the oil is 6:1 or more.

7. The process of claim 6, wherein the fat and/or oil reaction mixture contains less than 0.5 wt. % of free fatty acids.

8. The process of claim 6, wherein the fat and/or oil reaction mixture contains less than 0.1 wt. % of free fatty acids.

9. The process of claim 3, further comprising adding to the fat and/or oil reaction mixture a soluble catalyst.

10. The process of claim 9, wherein the soluble catalyst is an alkali metal or an alcoholate of an alkali metal.

11. The process of claim 1, further comprising adding to the fat and/or oil reaction mixture a catalyst comprised of a metal salt of an amino acid or an amino acid derivative, wherein the metal salt of the amino acid or the amino acid derivative is insoluble in alkanols and in the reaction mixture.

12. The process of claim 11, wherein the amino acid or amino acid derivative contains a quaternary nitrogen or a guanidino group.

13. The process of claim 12, wherein the metal salt of the amino acid or amino acid derivative is selected from the group consisting of calcium, strontium, barium alkaline-earth metal and heavy metal.

14. The process of claim 13, wherein the heavy metal is selected from the group consisting of silver, copper, zinc, manganese, iron, nickel, cobalt, lanthanum and rare-earth metal.

15. The process of claim 14, wherein the heavy metal salt of the amino acid or amino acid derivative is a zinc salt of arginine or a cadmium salt of arginine.

16. The process of claim 1, wherein the transesterification is carried out at a temperature ranging between 80° C. to 160° C.

17. The process of claim 1, wherein the transesterification is carried out at a temperature ranging between 100° C. to 150° C.

18. The process of claim 1, further comprising recirculating the alkanol fatty acid esters that remain behind as bottom products during the transesterification process.

19. A process for transesterification of a fat and/or an oil by means of alcoholysis, comprising:

forming a reaction mixture by adding at least six times the mol quantity of a monohydric alkanol to the fat and/or the oil;

adding 5 to 50 wt. % of at least one alkanol fatty acid ester;

adding a catalyst;

heating the reaction mixture to a temperature between 80° C. to 160° C.; and recirculating the alkanol fatty acid esters that remain behind as bottom products during the transesterification process, wherein the process results in a one-phase transesterification of the fat and/or the oil.

20. The process of claim 19, wherein the catalyst is soluble in the reaction mixture and further wherein the soluble catalyst is an alkali metal or an alcoholate of an alkali metal.

21. The process of claim 19, wherein the catalyst is comprised of a metal salt of an amino acid or an amino acid derivative, wherein the metal salt or the amino acid derivative is insoluble in alkanols and in the reaction mixture.

22. The process of claim 21, wherein the metal salt of the amino acid or amino acid derivative is selected from the group consisting of calcium, strontium, barium, another alkaline-earth metal and heavy metal.

23. The process of claim 22, wherein the heavy metal is selected from the group consisting of silver, copper, zinc, manganese, iron, nickel, cobalt, lanthanum and rare-earth metal.

24. The process of claim 23, wherein the amino acid or amino acid derivative contains a quaternary nitrogen or a guanidino group.

25. The process of claim 24, wherein the heavy metal salt of the amino acid or amino acid derivative is a zinc salt of arginine or a cadmium salt of arginine.

* * * * *